United States Patent [19]

Euteneuer

[11] Patent Number: 4,930,341
[45] Date of Patent: Jun. 5, 1990

[54] METHOD OF PREPPING A DILATATION CATHETER

[75] Inventor: Charles L. Euteneuer, St. Michael, Minn.

[73] Assignee: SciMed Life Systems, Inc., Maple Grove, Minn.

[21] Appl. No.: 323,686

[22] Filed: Mar. 15, 1989

[51] Int. Cl.⁵ .............................................. G01M 3/02
[52] U.S. Cl. .......................................... 73/37; 604/97; 73/40
[58] Field of Search ................. 73/37, 40; 604/97, 98, 604/100; 128/344

[56] References Cited

U.S. PATENT DOCUMENTS

| | | | |
|---|---|---|---|
| 4,212,192 | 7/1980 | Taylor | 73/49.1 |
| 4,522,194 | 6/1985 | Normann | 600/18 |
| 4,568,334 | 2/1986 | Lynn | 604/171 |
| 4,713,402 | 12/1987 | Solomon | 604/96 |
| 4,721,123 | 1/1988 | Cosentino et al. | 604/97 |

Primary Examiner—Hezron E. Williams
Attorney, Agent, or Firm—Kinney & Lange

[57] ABSTRACT

A method of testing a dilatation balloon catheter prior to use which comprises purging and priming the balloon catheter with a balloon protector in place about the balloon.

14 Claims, 3 Drawing Sheets

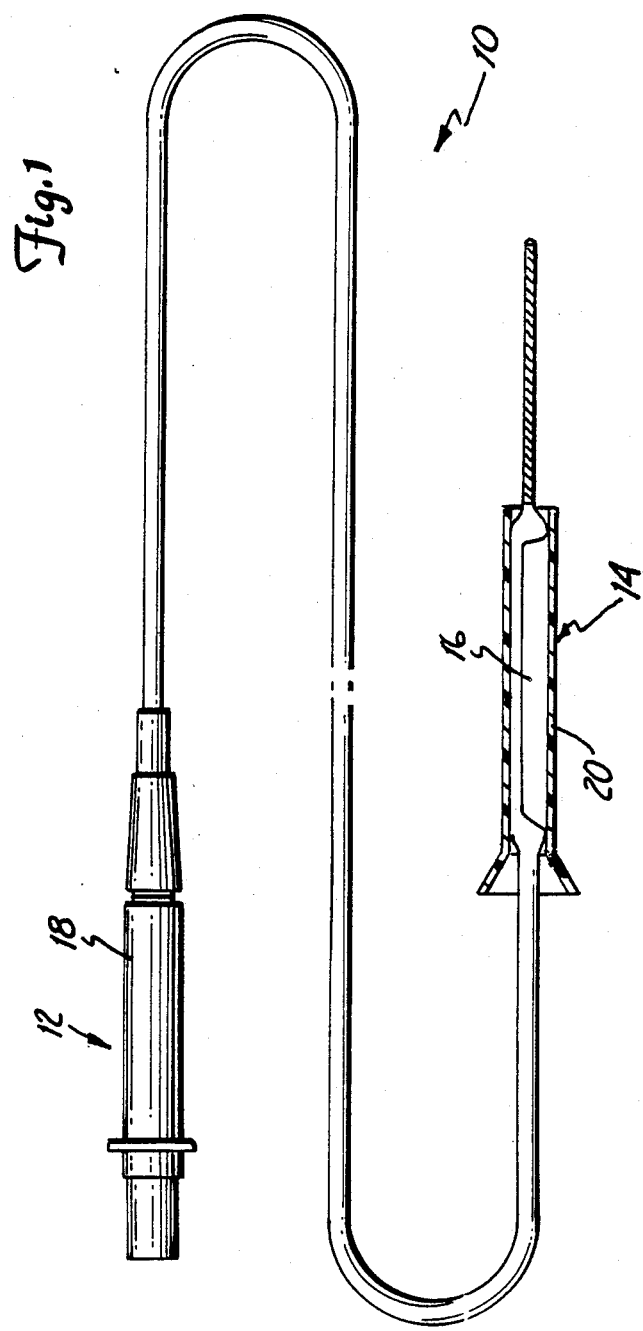

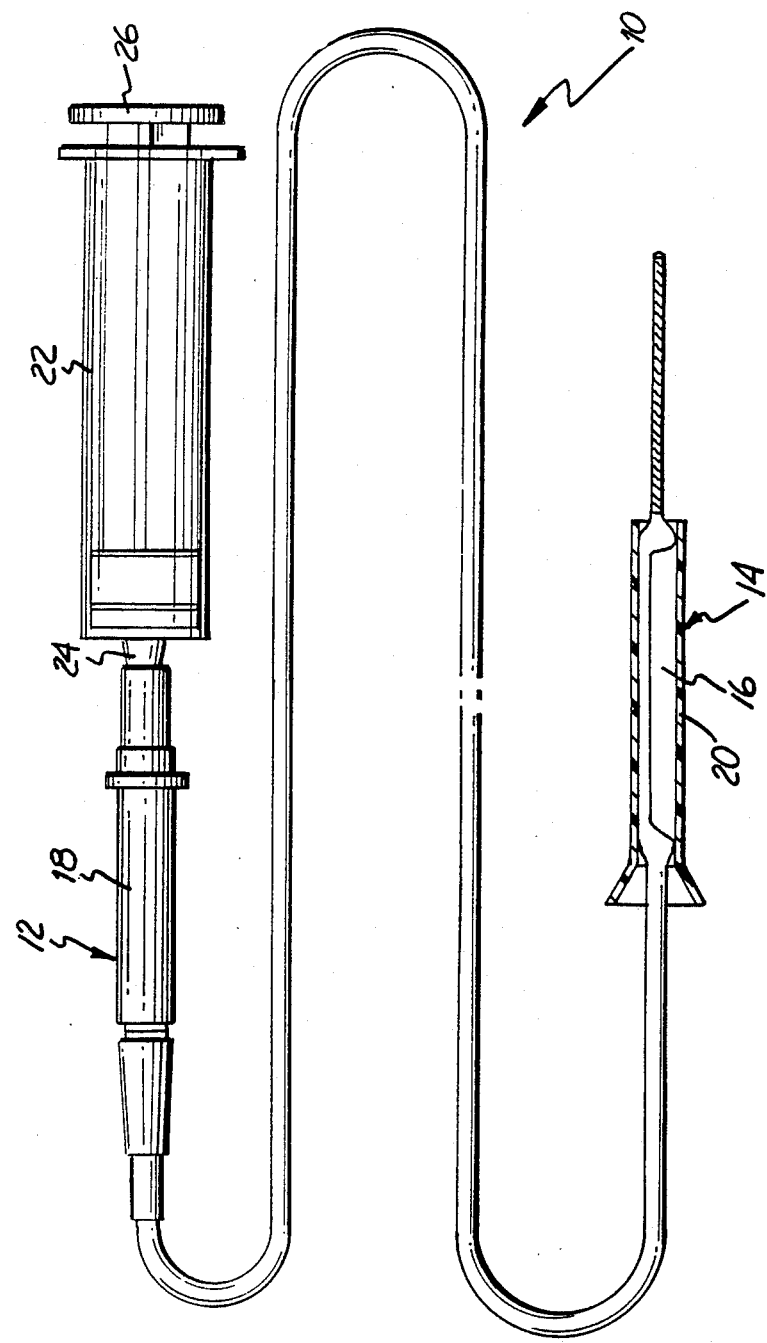

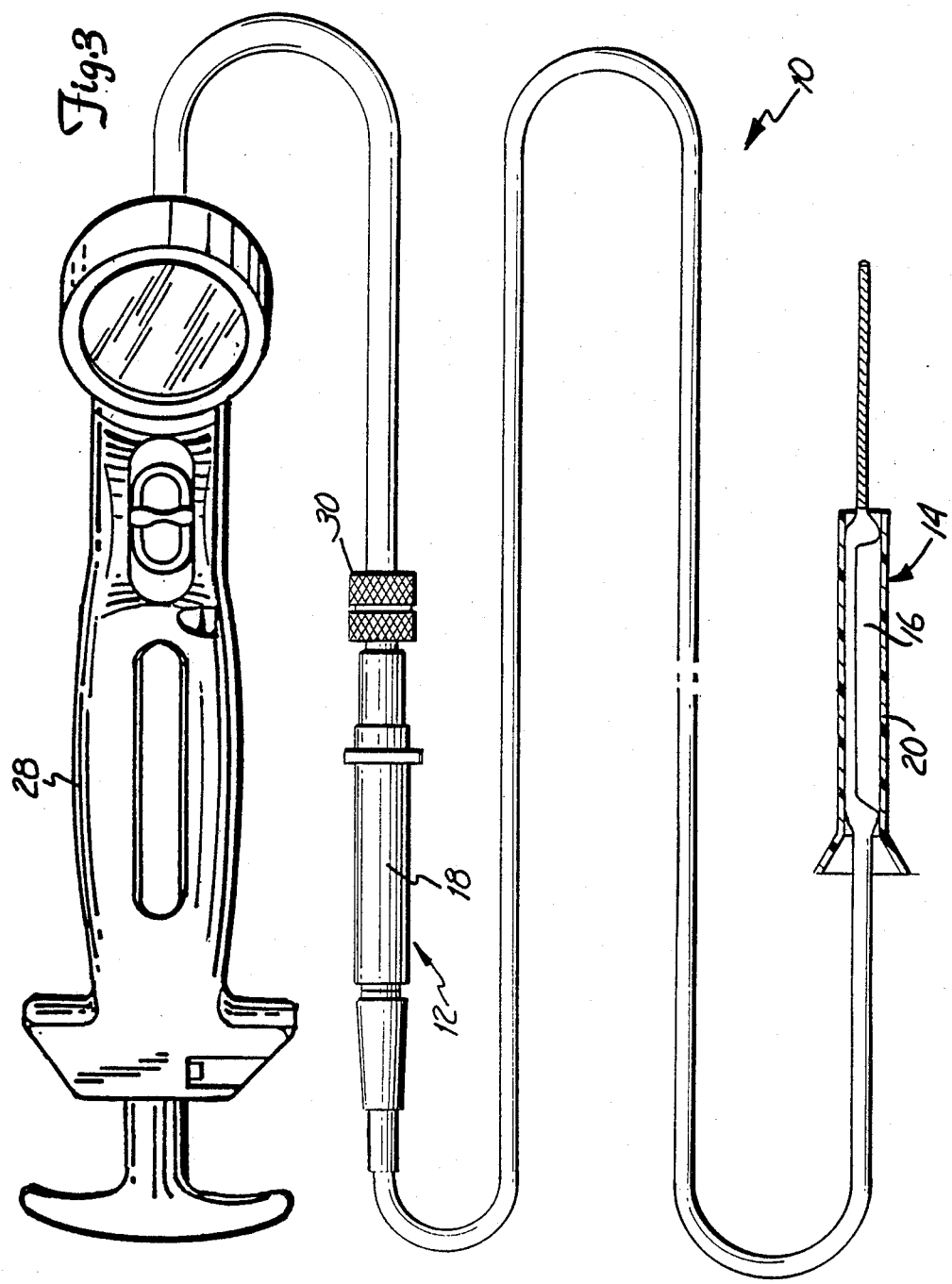

METHOD OF PREPPING A DILATATION CATHETER

BACKGROUND OF THE INVENTION

1. Field of the Invention

The present invention relates to the field of angioplasty. In particular, the present invention relates to dilatation balloon catheters which are insertable into a patient.

2. Description of the Prior Art

Angioplasty has gained wide acceptance in recent years as an efficient and effective method for treating certain types of vascular diseases. In particular, angioplasty is widely used for opening of stenosis in the coronary arteries, although it is also used for treatment of stenoses in other parts of the vascular system.

The most widely used form of angioplasty makes use of a balloon catheter which has an inflatable balloon at its distal end. Using fluoroscopy, the physician guides the catheter through the vascular system until the balloon is positioned across the stenosis. The balloon is then inflated by supplying fluid under pressure through an inflation lumen to the balloon. The inflation of the balloon causes stretching of the artery and pressing of the lesion into the artery wall to reestablish acceptable blood flow through the artery.

Before the balloon catheter can be used, it must be prepped. Prepping a balloon catheter includes purging the balloon of air and then pressure testing the balloon to check for leaks or a pressure drop. It is normal practice to remove the balloon protector before purging and priming the balloon.

SUMMARY OF THE INVENTION

The present invention is a method of prepping a dilation balloon catheter prior to use. The method involves priming the balloon catheter with the balloon protector in place about the balloon. The advantage of priming the balloon with the balloon protector in place is that the balloon can be pressure tested without expanding the balloon. Once the balloon of a balloon catheter is expanded, it is difficult or impossible to return the balloon to its pre-expansion profile. It is desirable to maintain the lowest balloon profile possible so that narrow arteries can be more easily negotiated by the balloon catheter. If the balloon is purged and pressure tested without the balloon protector in place, the balloon expands, and it is difficult to return the balloon to its pre-expansion profile. Therefore, the balloon has a larger profile which makes negotiating narrow arteries more difficult.

BRIEF DESCRIPTION OF THE DRAWINGS

FIG. 1 is a view of a balloon catheter with a balloon protector installed over the balloon.

FIG. 2 shows a syringe attached to the balloon catheter.

FIG. 3 shows an inflation device attached to the balloon catheter.

DETAILED DESCRIPTION OF THE PREFERRED EMBODIMENTS

A balloon catheter 10 is shown in FIG. 1. The catheter has a proximal end 12 and a distal end 14. At the distal end 14 is an inflatable balloon 16. At the proximal end 12 is an inflation manifold 18. The inflatable balloon 16 is encased by a balloon protector 20. The balloon protector 20 is normally applied to distal end 14 of catheter 10 during the manufacturing process, and remains in place during shipping and storage to prevent damage to the balloon 16. Balloon protector 20 is also used in the method of the present invention.

The balloon catheter 10 must be tested prior to use. In a preferred embodiment of the present invention, a 20 cc syringe 22 in FIG. 2 is filled with 2–3 cc of an inflation solution of 50% contrast medium and 50% saline. The syringe 22 has a nozzle 24 and a plunger 26. The balloon protector 20 is left in place over balloon 16. The syringe 22 is attached to the inflation manifold 18. The syringe 22 is held with the nozzle 24 pointing downward. A vacuum is then applied to the catheter 10 by pulling the syringe plunger 26 and holding it for at least 20 seconds. This allows any air in the catheter 10 to be drawn into the syringe 22. The plunger 26 is then slowly released. This allows the expelled air to be replaced with the inflation solution. The syringe 22 can then be removed from the catheter 10. It is then verified that there is a meniscus of the inflation solution in the inflation manifold 18.

An inflation device 28 in FIG. 3 is then filled with 2 cc of an inflation solution of 50% contrast medium and 50% saline. It is then verified that there is a meniscus of the inflation solution in the inflation device 28. A rotating adaptor 30 is attached between the inflation manifold 18 and the inflation device 28. The rotating adaptor 30 allows the catheter 10 to be rotated without the necessity of also rotating the inflation device 28.

With the balloon protector 20 still encasing the balloon 16, the inflation device 28 is used to apply positive pressure to the recommended maximum pressure to balloon 16. In a preferred embodiment, the recommended maximum pressure is 10 atmospheres. The balloon 16 (and the rest of catheter 10) is then examined for any leaks. If a leak exists, it may be seen visually, or it may be detected by a pressure drop in the pressure being applied by inflation device 28. This pressure drop can be read on the pressure gauge which is a part of inflation device 28. If the balloon 16 exhibits no visible leaks or pressure drop, the pressure may be released.

The inflation device 28 is then used to apply and maintain a vacuum to the balloon 16. The balloon protector 20 is removed when the catheter 10 is ready to be used.

In an alternative embodiment, the inflation device 28 is used instead of the syringe 22 to purge the catheter 10 of air.

Although the present invention has been described with reference to preferred embodiments, workers skilled in the art will recognize that changes may be made in form and detail without departing from the spirit and scope of the invention.

What is claimed is:

1. A method of preparing a dilatation catheter prior to use in an angioplasty procedure, the method comprising:
   providing the dilatation catheter with a balloon protector over a balloon at a distal end of the catheter with the balloon being in an initial uninflated state;
   priming the balloon with the balloon protector in place over the balloon, whereby the balloon protector maintains the balloon in its uninflated state during priming; and removing the balloon protector from the distance end of the catheter.

2. The method of claim 1 wherein priming the balloon includes the step of pressurizing the balloon.

3. The method of claim 1 wherein priming the balloon includes the step of applying a vacuum to the balloon.

4. A method for preparing a dilatation catheter for angioplasty use, wherein the catheter has a shaft with a proximal end and a distal end, an inflatable balloon at the distal end, and a removable balloon protector covering the balloon, the method comprising the steps of:
applying a vacuum through the shaft to the balloon while the balloon protector is in place over the balloon;
pressurizing the balloon while the balloon protector is in place over the balloon and the balloon is in an uninflated state, with the balloon protector maintaining the balloon in its uninflated state;
again applying a vacuum to the balloon while the balloon protector is in place over the balloon; and
removing the balloon protector from the balloon.

5. The method of claim 4, and further comprising the step of:
inspecting the catheter, during pressurizing, for leaks and pressure drops.

6. A method of testing a dilatation balloon catheter prior to use, the catheter having a shaft with a fluid coupling at a proximal end and inflatable balloon at a distal end, the method comprising:
connecting an inflation device containing inflation solution to the fluid coupling; and
pressurizing the balloon catheter using inflation solution from the inflation device while a balloon protector is in place on the balloon and the balloon is in an uninflated state, with the balloon protector maintaining the balloon in its uninflated state.

7. The method of claim 6 wherein the pressurizing step includes:
applying to the balloon a predetermined pressure; and
checking the catheter and inflation device for visible leaks and loss of pressure.

8. The method of claim 7 wherein the predetermined pressure is about 10 atmospheres.

9. The method of claim 6 and further comprising:
applying and maintaining a vacuum to the balloon through the inflation device.

10. The method of claim 9 and further comprising the step of:
removing the balloon protector from the distal end of the catheter prior to use of the catheter.

11. The method of claim 7 wherien the solution contains saline and a contrast medium.

12. The method of claim 6, wherein prior to pressurizing, the method further comprises the steps of:
connecting a first source of inflation solution to the fluid coupling;
applying a vacuum to the balloon by use of the source while the balloon protector is in place on the balloon; and
releasing the vacuum.

13. The method of claim 12 wherein the first source is a syringe.

14. The method of claim 12 wherein the first source is an inflation device.

* * * * *

UNITED STATES PATENT AND TRADEMARK OFFICE
CERTIFICATE OF CORRECTION

PATENT NO. : 4,930,341

DATED : June 5, 1990

INVENTOR(S) : CHARLES L. EUTENEUER

It is certified that error appears in the above-identified patent and that said Letters Patent is hereby corrected as shown below:

Column 1, line 3, after the title, please insert:

This Application claims the benefit, pursuant to 35 U.S.C. § 120, of the filing date of Application Serial No. 120,366, filed November 13, 1987 (issued July 11, 1989 as U.S. Patent No. 4,846,174), which is a Continuation In-Part of Application Serial No. 894,658 filed August 8, 1986 (abandoned).

Col. 2, delete lines 61-64, and insert the following:

providing the dilatation catheter with a balloon protector over a
    balloon at a distal end of the catheter with the balloon being
    in an initial uniflated state;

Col. 3, line 1, delete "distance", and insert --distal--.

Signed and Sealed this

Thirty-first Day of August, 1993

*Attest:*

BRUCE LEHMAN

*Attesting Officer*     *Commissioner of Patents and Trademarks*